(12) United States Patent
Engeberg et al.

(10) Patent No.: US 9,744,055 B2
(45) Date of Patent: Aug. 29, 2017

(54) ANTAGONISTICALLY ACTUATED SHAPE MEMORY ALLOY MANIPULATOR

(71) Applicants: Erik D. Engeberg, Boca Raton, FL (US); Savas Dilibal, Akron, OH (US)

(72) Inventors: Erik D. Engeberg, Boca Raton, FL (US); Savas Dilibal, Akron, OH (US)

(73) Assignee: The University of Akron, Akron, OH (US)

( * ) Notice: Subject to any disclaimer, the term of this patent is extended or adjusted under 35 U.S.C. 154(b) by 44 days.

(21) Appl. No.: 14/683,867

(22) Filed: Apr. 10, 2015

(65) Prior Publication Data
US 2015/0289994 A1 Oct. 15, 2015

Related U.S. Application Data

(60) Provisional application No. 61/977,822, filed on Apr. 10, 2014.

(51) Int. Cl.
| | |
|---|---|
| A61F 2/54 | (2006.01) |
| A61F 2/70 | (2006.01) |
| A61F 2/58 | (2006.01) |
| F03G 7/06 | (2006.01) |
| B25J 9/14 | (2006.01) |
| B25J 9/12 | (2006.01) |
| B25J 15/12 | (2006.01) |

(52) U.S. Cl.
CPC .............. *A61F 2/586* (2013.01); *B25J 9/12* (2013.01); *B25J 9/142* (2013.01); *B25J 15/12* (2013.01); *F03G 7/065* (2013.01); *G05B 2219/39486* (2013.01)

(58) Field of Classification Search
CPC ............................ A61F 2/586; A61F 2002/587
See application file for complete search history.

(56) References Cited

U.S. PATENT DOCUMENTS

| | | | | |
|---|---|---|---|---|
| 6,408,289 | B1 * | 6/2002 | Daum | A61F 2/586 |
| | | | | 706/44 |
| 2014/0306473 | A1 * | 10/2014 | Koehler | F03G 7/065 |
| | | | | 294/192 |

FOREIGN PATENT DOCUMENTS

| | | | | |
|---|---|---|---|---|
| GB | 2 106 190 A | * | 4/1983 | F03G 7/065 |

* cited by examiner

*Primary Examiner* — David H Willse
(74) *Attorney, Agent, or Firm* — Renner, Kenner, Greive, Bobak, Taylor & Weber Co. LPA

(57) ABSTRACT

An antagonistically actuated shape memory alloy (SMA) manipulator utilizes a pair of SMA actuators. The SMA actuators are configured, such that one actuator is trained to have a substantially linear or extended shape in its austenite phase, while the other actuator is trained to have a curved or flexed shape in its austenite phase. As such, the manipulator is operated, such that when one SMA actuator is heated and takes on its "trained" shape in the austenite phase, the other SMA actuator is permitted to cool and allowed to return to its original "untrained" shape in the martensite phase, and vice versa. This antagonistic operation of the SMA actuators allows the manipulator to achieve rapid flexion and extension movements.

22 Claims, 6 Drawing Sheets

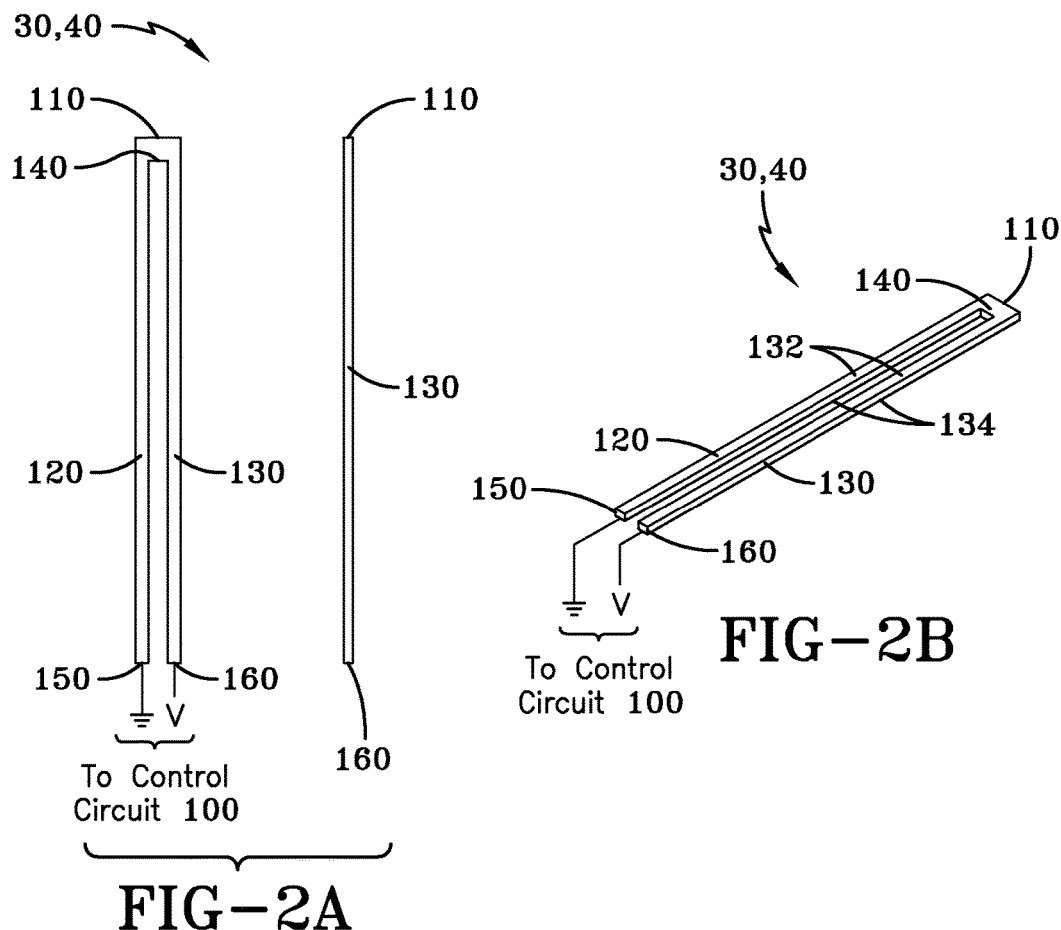
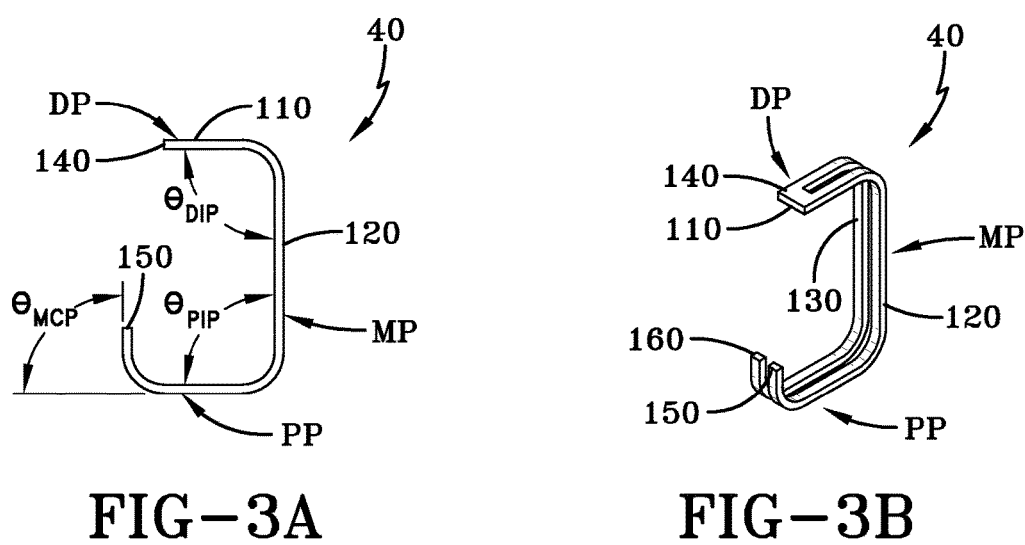

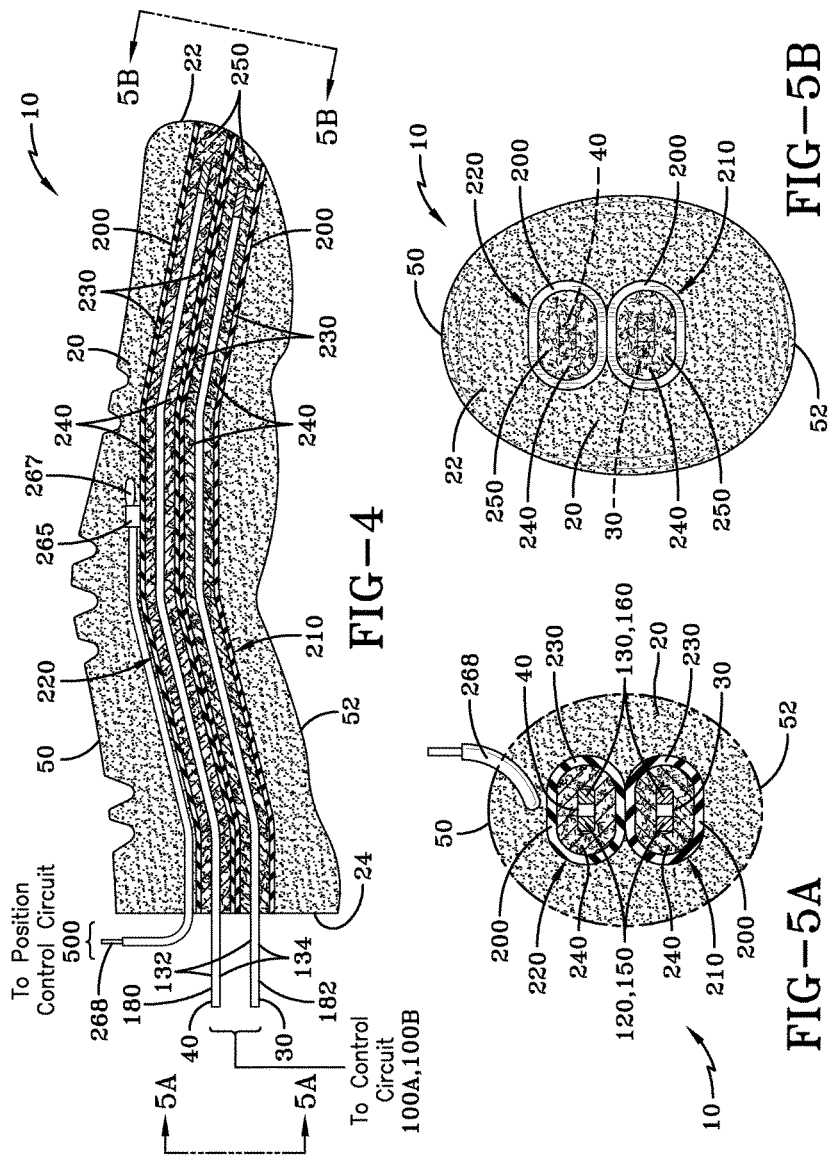

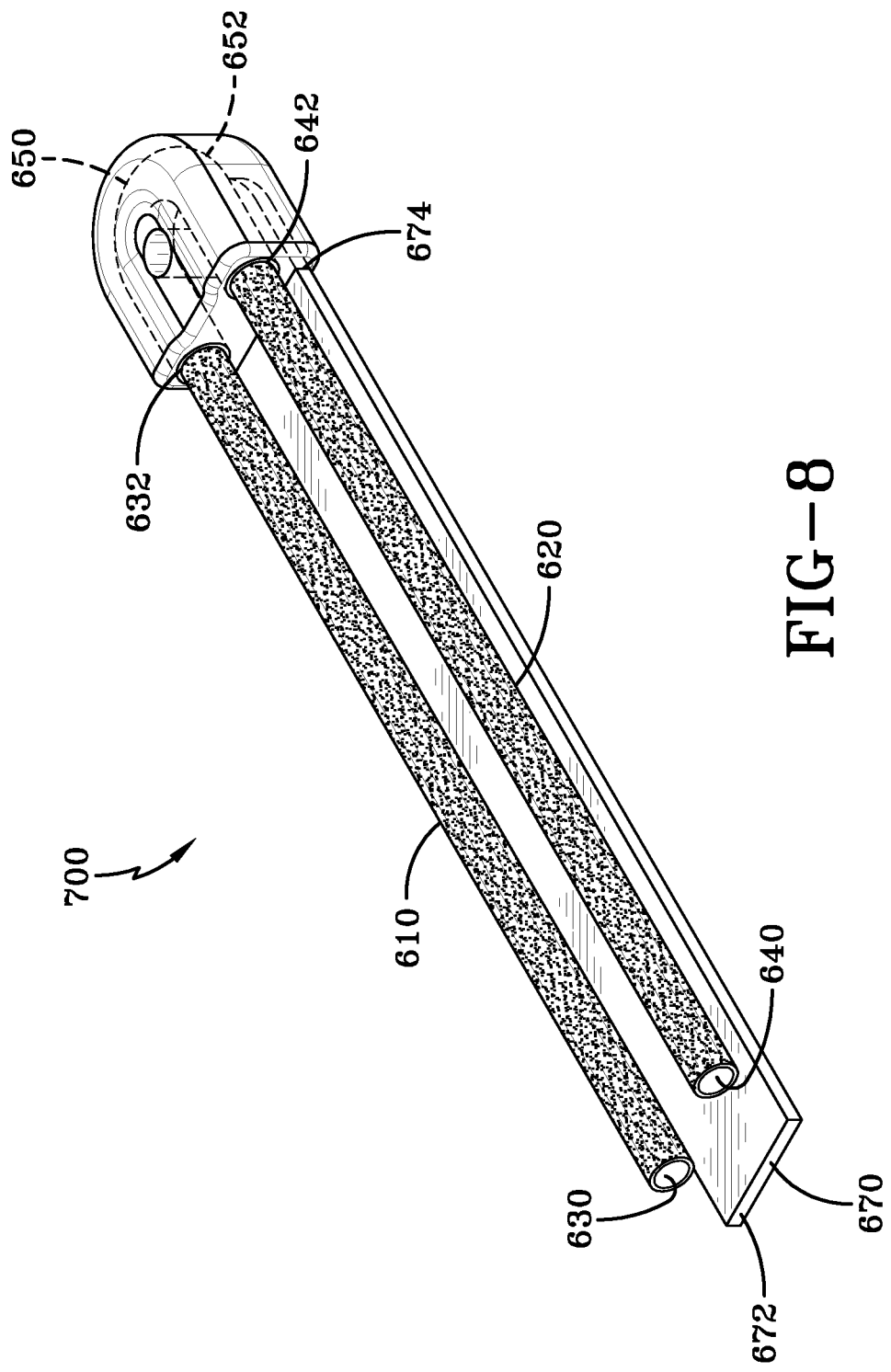

ANTAGONISTICALLY ACTUATED SHAPE MEMORY ALLOY MANIPULATOR

CROSS-REFERENCE TO RELATED APPLICATION

This application claims the benefit of U.S. Provisional Application No. 61/977,822 filed Apr. 10, 2014, the contents of which are incorporated herein by reference.

STATEMENT REGARDING FEDERALLY SPONSORED RESEARCH OR DEVELOPMENT

This invention was made with government support under Contract IIP 1265145 awarded by The National Science Foundation. The government has certain rights in the invention.

TECHNICAL FIELD

Generally, the present invention relates to manipulation devices. Particularly, the present invention relates to manipulation devices, which use shape memory alloy (SMA). More particularly, the present invention relates to a manipulator device that moves by antagonistically controlled shape memory alloy (SMA) actuators.

BACKGROUND OF THE INVENTION

Due to their lightweight, as well as their reduced size and complexity, shape memory alloy (SMA) manipulators or actuators provide numerous advantages over traditional motor-based actuators. For example, SMA actuators have been used in a variety of robotic applications, such as in the case of micro-manipulators, pumps, bio-inspired inchworms, biomimetic fish, and robotic octopi, for example. In addition, SMA actuators have been utilized in robotic hands, whereby wires formed of SMA are attached across the joints of the robotic fingers to control their movement. In such robotic hand applications, the fingers of the robotic hand are actuated by heating the SMA wire, which results in the flexion or the extension of the finger joint. In addition, some robotic hands are designed to be actuated by SMA wires via a finger tendon drive system, whereby the SMA wires are positioned in series with the linear springs or through segmented binary control. SMA actuators have also been used in conjunction with DC (direct current) motors for hybrid actuation of an artificial finger and a surgical manipulator.

In order to control an SMA actuator, it must be heated in order to cause it to transition from an initial "untrained" shape (martensite phase) to a second predetermined or "trained" shape (austenite phase), and then subsequently cooled so that the SMA actuator returns back to its initial shape (martensite phase). During the heating phase, SMA actuators have a fast response time, whereby they can reach their austenite phase or their "trained" shape very rapidly. However, one problem with SMA-based robotic hands is that the SMA actuators require a lengthy amount of time to cool down so that the actuator can return to its initial "untrained" shape in its martensite phase. This slow transition time between the "memory" or "trained" shape in its austenite phase, back to the "untrained" shape in its martensite phase results in a low-bandwidth system, which limits the use of the SMA actuators in various applications, such as robotics, such as in prosthetics limbs and hands.

Due to the low-bandwidth operation of the SMA actuators in robotic or prosthetic devices, several attempts have been made to overcome this obstacle. For example, a differential pulley system has been developed, which uses antagonistic SMA wires, whereby opposing SMA wires drive the joint in either direction. This increases the response speed of the SMA robotic system, as compared to conventional SMA robotic systems that utilize a return spring to facilitate the movement of the SMA actuator from the memory/trained shape of its autenite phase, back to its initial shape of its martensite phase. However, while such differential pulley-based robotic systems have improved operating performance, they are complex, and as a result, require frequent maintenance and repair, which is undesirable. However, while such antagonistic SMA robotic systems have improved response speed, such systems could achieve further improvements in operating performance if the SMA wires used thereby were cooled in an efficient manner.

Therefore, there is a need for a manipulator that uses antagonistically controlled shape memory alloy (SMA) actuators to control its movement. There is also a need for a manipulator that uses antagonistically controlled shape memory alloy (SMA) actuators, which are cooled by liquid such as water to increase the speed of the manipulator to move from its austenite phase to its martensite phase. In addition, there is a need for an antagonistic shape memory alloy (SMA) manipulator or actuator for a prosthesis, such as prosthetic finger of a prosthetic hand, which has an enhanced cooling system. Additionally, there is a need for an antagonistic SMA actuator for a prosthesis, such as a prosthetic finger, which has individual cavities that are configured to carry antagonistically orientated SMA actuators therein, whereby one actuator is trained to have a flexion shape in its austenite phase and the other actuator is trained to have an extension shape in its austenite phase. Furthermore, there is a need for an antagonistic SMA actuator for a prosthetic finger, which includes ports to allow water to enter and exit prosthetic finger, so as to cool the SMA actuator, when the prosthetic finger is submerged in water.

SUMMARY OF THE INVENTION

In light of the foregoing, it is a first aspect of the present invention to provide a manipulator device that includes a first shape memory alloy (SMA) actuator that is configured to take on a predetermined shape orientation when in an austenite phase; and a second shape memory alloy (SMA) actuator that is configured to take on a predetermined shape orientation when in the austenite phase; wherein the predetermined shape orientation of the first SMA actuator in the austenite phase is antagonistic to the predetermined shape orientation of the second SMA actuator in the austenite phase.

BRIEF DESCRIPTION OF THE DRAWINGS

These and other features and advantages of the present invention will become better understood with regard to the following description, appended claims, and accompanying drawings wherein:

FIG. 2A is an elevational view of a plate formed of SMA, which forms the extensor and flexor actuators used to control the movement of the prosthetic finger in accordance with the concepts of the present invention;

FIG. 2B is a perspective view of the SMA plate shown in FIG. 2A in accordance with the concepts of the present invention;

FIG. 3A is an elevational view of the flexor actuator when bent in an orientation for thermal memory training to set its autensite shape in accordance with the concepts of the present invention;

FIG. 3B is a perspective view of the flexor actuator of FIG. 3A in accordance with the concepts of the present invention;

FIG. 4 is a cross-sectional view of the prosthetic finger, which includes the flexor and extensor actuators in accordance with the concepts of the present invention;

FIG. 5A is an elevation view of the end or base of the prosthetic finger in the direction of 5A-5A of FIG. 4 in accordance with the concepts of the present invention;

FIG. 5B is a cross-sectional view of the tip of the prosthetic finger in the direction of 5B-5B of FIG. 4 showing water inlet ports in accordance with the concepts of the present invention;

FIG. 8 is a perspective view of an alternative embodiment of the shape memory alloy manipulator in accordance with the concepts of the present invention.

DETAILED DESCRIPTION OF THE INVENTION

Figure 1A:
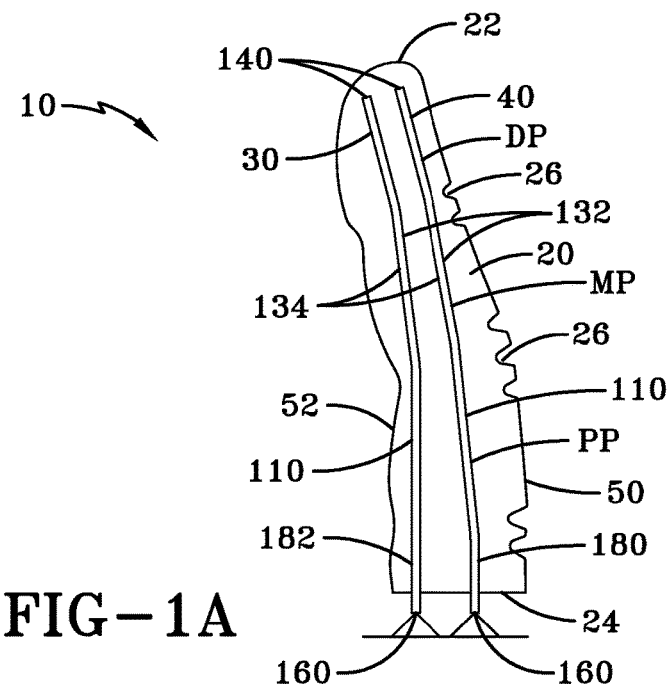
FIG. 1A is a schematic view of a prosthetic finger that includes antagonistically controlled, extensor and flexor, shape memory alloy (SMA) actuators, which are both cooled and are in their martensite phase in accordance with the concepts of the present invention.
Figures 1B, 1C:
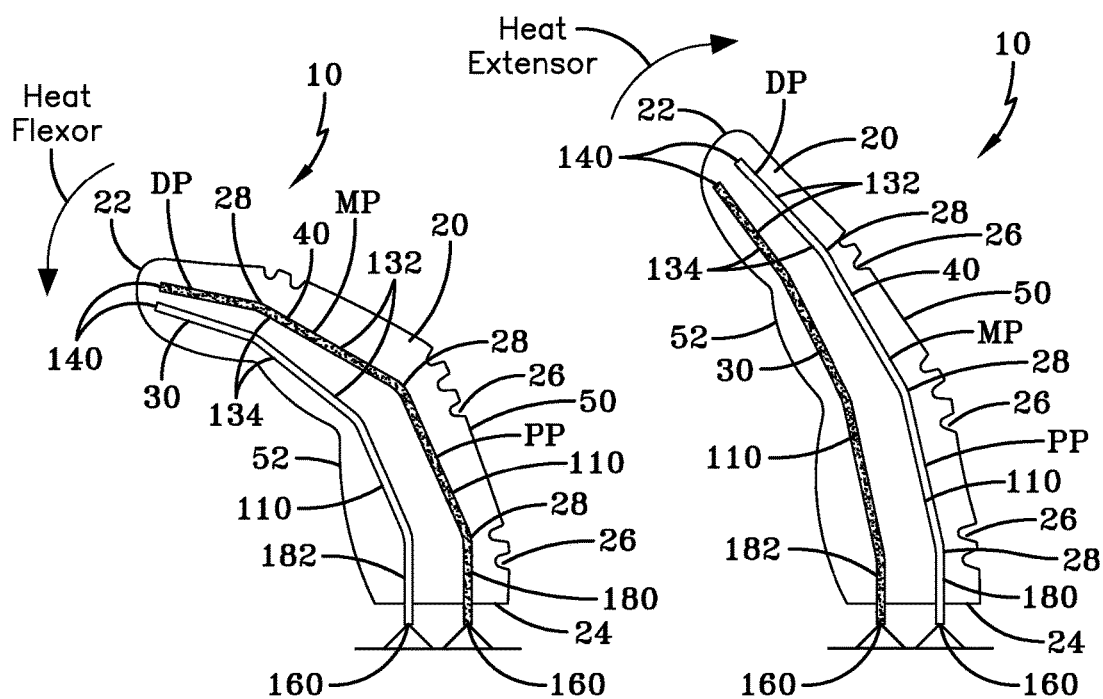
FIG. 1B is a schematic view of the prosthetic finger of FIG. 1A, whereby the flexor SMA actuator is heated, while the extensor actuator remains cool, so as to cause the prosthetic finger to move into a flexed state or orientation in accordance with the concepts of the present invention.
FIG. 1C is a schematic view of the prosthetic finger of FIG. 1A, whereby the extensor SMA actuator is heated, while the flexor actuator remains cool, so as to cause the prosthetic finger to move into an extended state or orientation in accordance with the concepts of the present invention.

An antagonistically actuated shape memory alloy (SMA) manipulator, which is embodied as a prosthetic or robotic manipulator, is generally referred to by numeral 10, as shown in FIGS. 1A-C of the drawings. That is, while the SMA manipulator 10 is discussed herein as comprising a prosthetic finger device, the SMA manipulator 10 may be implemented as a robotic device as well, and may be utilized in any suitable environment or used in any desired application. In particular, the prosthesis 10 discussed herein relates to prosthetic fingers, however the structural components utilized by the prosthetic finger 10 to be discussed, may be readily adapted for use in any prosthetic joint or limb. The prosthesis 10 includes a prosthetic body 20 that is formed of any suitable flexible material, such as two-part soft liquid rubber for example. Positioned within the prosthetic body 20 are an extensor actuator 30 and a flexor actuator 40, which are both formed of shape memory alloy (SMA). The extensor and flexor actuators 30, 40 are mechanically linked together via the flexible prosthetic body 20, and operate to move the prosthetic body 20 between flexed and extended positions. In particular, the extensor actuator 30 is configured, such that it takes on a substantially straight or linear shape (i.e. extended shape) in its austenite phase, when it is Joule heated, while the flexor actuator 40 is configured, such that it takes on a curved shape (i.e. flexed shape) in its austenite phase when it is Joule heated. Thus, movement of the prosthetic finger 10 between a fully flexed position and a fully extended position, is achieved by antagonistically controlling the extensor and flexor actuators 30, 40, using a nonlinear antagonistic controller 100 to be discussed in detail below. That is, the prosthetic finger 10 operates, such that when the flexor actuator 40 is heated, and the extensor actuator 30 is permitted to cool, the prosthetic finger 10 is moved into a curved orientation/shape; and when the extensor actuator 30 is heated, and the flexor actuator 40 is permitted to cool, the prosthetic finger 10 is moved back to an extended or straight orientation/shape.

The prosthetic body 20 is formed substantially in the shape of a finger and extends from a tip 22 to a base 24. In addition, the prosthetic body 20 forming the finger 10 includes strain reliefs 26 that are configured to be respectively aligned with the pivot points 28 in the flexor actuator 40 which enable the proximal phalanx PP, the middle phalanx MP, and the distal phalanx DP of the flexor actuator 40 to rotate through respective angles $\theta_{MCP}$, $\theta_{PIP}$, and $\theta_{DIP}$, shown in FIG. 3A.

In order to control the movement of the prosthetic finger body 20 in an anthropomorphic manner, the extensor and flexor actuators 30 and 40 are disposed within the body 20 in a stacked manner, such that the flexor actuator 40 is positioned proximate to a dorsal or upper surface 50 of the finger body 20, and the extensor actuator 30 is positioned proximate to a palmar or bottom surface 52 of the finger body 20. However, it should be appreciated that the position of the extensor and flexor actuators 30, 40 may be reversed.

With regard to the extensor and flexor actuators 30 and 40, they are each formed of a shape memory alloy (SMA) plate 110, as shown in FIGS. 2A-B. The plate 110 forming each of the SMA actuators 30, 40, is configured as a continuous section of solid SMA material, which has elongated sections 120 and 130, which are each joined at one end by a base section 140 that extends in a substantially transverse direction to the sections 120 and 130. In addition, the plate 110 is formed to have a substantially rectilinear cross-sectional shape, such as a square or rectangle. However, any suitable cross-sectional shape may be used. As such, each of the elongated sections 120 and 130 are terminated at respective free ends 150 and 160. The free ends 150 and 160 of the plates 110 that are used to form the extensor actuator 30 and the flexor actuator 40 are coupled to the control circuit 100 to be discussed in detail below. As such, the elongated sections 120 and 130 of the actuators 30, 40 have an upper surface 132 and a lower surface 134, whereby the upper surface 132 of the actuators 30, 40 is proximate to the dorsal surface 50 of the finger body 20, and the lower surface 134 of the actuator 30, 40 is proximate to the palmar surface 52 of the finger body 20.

It should be appreciated that in some embodiments, the actuators 30 and 40 may comprise SMA plates 110 that are solid, hollow, or a combination of both. In further embodiments, the actuators 30 and 40 may comprise wires, films, tapes, ribbons and tubes formed of SMA material instead of the plates discussed above.

In order to enable the antagonistic operation of the extensor actuator 30 and the flexor actuator 40, the SMA plates 110 used to form each of the actuators 30, 40 must be thermally trained, so that that when the plates 110 are heated, they take on their "trained" or "memory" shape in their austenite phase. It should be appreciated, that the extensor actuator 30 and the flexor actuator 40 refers to the particular SMA plate 110 that is trained for use in carrying out the flexing and extending movements of the prosthetic finger 10.

Thus, the SMA plate 110 that is used to form the extensor actuator 30 is thermally trained to have a substantially straight or linear shape in its austenite phase when Joule heated, which operates to extend the prosthetic finger 10 outward, as shown in FIG. 1C. It should be appreciated that the SMA plate 110 used to form the extensor actuator 30 may be thermally trained using any suitable technique.

In addition, to train the flexor actuator 40 to move, so as to take on a bent shape in its austenite phase when Joule heated, as shown in FIG. 1B, the SMA plate 110 used to form the flexor actuator 40 is placed into a mold, such as a mold formed from aluminum or other rigid material. Once the flexor actuator 40 is placed in the mold, the mold and the actuator 40 are placed in a furnace, such as furnace model ST-1150C-458 that is provided by Sentro Tech Corp., Cleveland, USA, and heat treated for approximately 8 minutes at about 600° C. Afterward, the SMA flexor actuator 40 is water quenched. This thermal training process allows the flexor actuator 40 to take the bent shape shown in FIGS. 3A-B, when Joule heated above its phase transition temperature. In one aspect, the flexor actuator 40 may be configured, such that it attains a bent shape, which mirrors the phalanges of a human finger in its austenite phase. For example, the plate 110 of the flexor actuator 40 may have a shape in its austenite phase, which includes a proximal phalanx PP section, middle phalanx MP section, and a distal phalanx DP section (mimicking a human finger) that are each permitted to move or bend at pivot points 28 about respective angles of rotation $\theta_{MCP}$, $\theta_{PIP}$, and $\theta_{DIP}$, as shown in FIGS. 3A-B. In one embodiment, the flexor actuator 40 may have a total length of about 85 mm, whereby the length of the proximal phalanx PP is about 39.02 mm, the length of the middle phalanx MP is about 23.03 mm, and the length of the distal phalanx DP is about 17.95 mm. However, it should be appreciated that total length of the flexor actuator 40, as well as that of the PP, MP, and DP sections may take one any suitable length. In addition, a base section 180 that extends from the end of the proximal phalanx PP to the free ends 150,160 of the plate 110, serves as a proximal base, which is used to attach the actuator 40 to a rigid support structure, such as a prosthetic hand or the like. In one embodiment, the base section 180 may be about 5 mm in length, however any suitable length may be used. It should also be appreciated that the thermal training process can impart a curved shape, rather than the finger-like shape shown in the Figs.

Similarly, the extensor actuator 30 may be configured to have any suitable length, such as about 85 mm for example. In one aspect, the length of the extensor actuator 30 and the flexor actuator 40 may be of the same length. It should also be appreciated that the extensor actuator 30 may be configured to include a base section 182, which is adjacent to the free ends 150, 160 of the plate 110 of the extensor actuator 30, and is suitable for attaching the actuator 30 to a rigid structure, such as a prosthetic hand or the like. In one embodiment, the base section 182 may have a length of about 5 mm, however any suitable length may be used.

The SMA actuators 30 and 40 may be formed from any suitable shape memory alloy (SMA) material, including but not limited to, polycrystalline NiTi and polycrystalline ternary NiTiCu. In one aspect, the NiTi SMA material, designated as $NiTi_1$, may have a $Ni_{50.1}Ti_{49.9}$ atomic weight composition. In another aspect, the NiTi SMA material, designated as $NiTi_2$, may have a $Ni_{49.78}Ti_{50.22}$ atomic weight composition. The $NiTi_1$ and $NiTi_2$ SMA materials may have a thickness of about 1 mm, which are provided by Memry (Weil am Rhein, Germany). In one aspect, the NiTiCu material may have a $Ni_{50}Ti_{40}Cu_{10}$ atomic weight composition, and a thickness of about 1 mm, which be provided by Kellogg's Research Labs (Moultonborough, USA). However, it should be appreciated that the SMA actuators 30 and 40 may be formed of any suitable SMA material, which is of any suitable thickness, dimension, and cross-sectional shape. Thus, all of the SMA materials that are used to form the SMA actuators 30 and 40 are configured so that their martensite phase is achieved at room temperature, whereby upon Joule heating, a reverse phase transformation occurs, whereupon the SMA actuators 30, 40 enter the austenite phase to take on their "trained" or "memory" shape. The austenite finish temperature ($A_f$) for each of the SMA alloys discussed above are shown in Table 1.

TABLE 1

| SMA material properties and results from thermal shape training. | | | | | | | |
|---|---|---|---|---|---|---|---|
| Material | Composition | Af Temp. | Angles (rad) | | | Max Force (N) | Compliant Object |
| | | | $\theta_{MCP}$ | $\theta_{PIP}$ | $\theta_{DIP}$ | (N) | (N) | (mm) |
| $NiTi_1$ | $Ni_{50.1}Ti_{49.9}$ | 69° C. | 1.26 | 1.31 | 1.08 | 9.01 ± 0.19 | 1.85 ± 0.02 | 11.29 ± 0.21 |
| $NiTi_2$ | $Ni_{49.78}Ti_{50.22}$ | 96° C. | 0.66 | 1.19 | 0.98 | 5.82 ± 0.66 | 1.28 ± 0.02 | 7.80 ± 0.58 |
| NiTiCu | $Ni_{50}Ti_{40}Cu_{10}$ | 45° C. | 0.63 | 1.15 | 0.94 | 5.46 ± 0.48 | 0.74 ± 0.05 | 3.03 ± 0.92 |

The prosthetic finger 10 is configured so that the finger body 20 and the actuators 30,40 bend or flex together as an integrated unit, so as to move the prosthetic finger 10 in a manner that substantially mimics the anthropomorphic movement of a human finger. To accomplish this, the finger body 20 includes an actuator cavity 200, which extends the length of the finger body 20, as shown in FIG. 4. Disposed within the actuator cavity 200 are barrier tubes 210 and 220, which are respectively associated with the extensor and the flexor actuators 30, 40. The barrier tubes 210 and 220 extend the length of the finger body 20 from the tip 22 to the base 24. The barrier tubes 210, 220 each include an outer dielectric tube 230 and an inner thermal insulating tube 240, such that the inner and outer tubes 230, 240 are concentrically or co-axially arranged with respect to each other. The dielectric tube 230 may be formed of any suitable material that is electrically non-conductive, such as silicone or rubber for example, and serves to electrically isolate each of the actuators 30, 40 from each other. The thermal insulating tube 240, which comprises thermal insulation, such as T117EA4B (Delfingen, Rochester Hill, USA), serves to thermally isolate heat that is generated from the actuators 30, 40 during the operation of the prosthetic finger 10, from the material that is used to form the finger body 20. It should also be appreciated that the ends of the thermal insulating tubes 240 in each of the barrier tubes 210, 220 extends to the tip 22 of the finger body 20, such that end of the thermal insulating tubes 240 that are proximate to the tip 22 of the prosthetic finger 20 are each fluidly coupled to an associated port 250 that is disposed in the tip 22 of the prosthetic finger 10. As such, the port 250 opens to the outside environment to allow fluid, such as water, to enter and exit each of the thermal insulating tubes 240 provided by the barrier tubes 210, 220. As such, the flexion and extension movements of the prosthetic finger 10, serves to force cooling water through the insulating tubes 240, which has entered via the ports 250. Such movement of the water in and out of the insulating tubes 240 via the ports 250 allows for the rapid cooling of each of the actuators 30 and 40, thereby increasing the operational bandwidth of the prosthetic finger 10.

Figure 6:
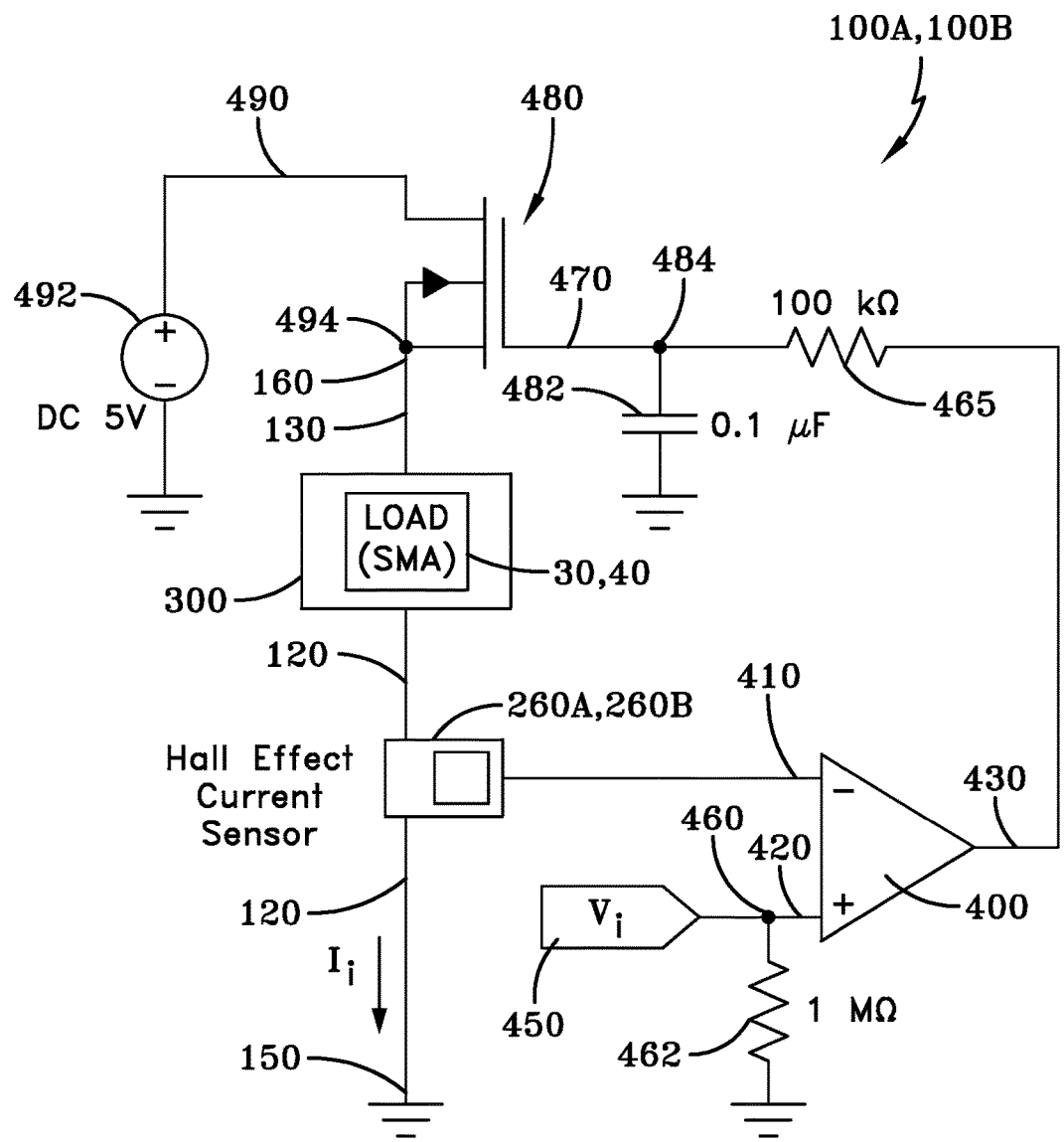
FIG. 6 is a schematic diagram of a current control circuit for use with both the extensor actuator and the flexor actuator of the prosthetic finger in accordance with the concepts of the present invention.

In addition, to measure the flow of electrical current in the actuators 30 and 40, a hall-effect sensor 260A is connected to the section 120 of the extensor actuator 30 and a hall-effect sensor 260B is connected to the section 120 of the flexor actuator 40, as shown in FIG. 6. In one aspect, the hall-effect sensors 260A-B may comprise model ACS712, which is provide by Allegro MicroSystems.

In order to measure the position of the finger 10, as it moves between extended and flexed positions, a hall-effect position sensor 265 and magnet 267 are located near the proximal interphalangeal (PIP) joint of the finger 10. Specifically, the position sensor 265 is located proximate to the flexor actuator 40 and the magnet 267 is positioned distal to the sensor 265. In one aspect, the sensor may comprise model A1321, which is provided by Allegro MircoSystems. In order to interface the hall-effect position sensor 265 with the position control circuit 500 to be discussed, wires 268 are used.

The prosthesis 10 also includes the control circuit or system 100, which is configured to supply electrical current to each of the actuators 30 and 40. The control system 100 includes a substrate 300, such as a conventional electrical circuit board, which may be formed of any suitable material, such as fiberglass for example. It should be appreciated that the substrate may comprise the structure of a prosthetic hand or arm, or the like. The actuators 30 and 40 are rigidly attached to the substrate using any suitable means of fixation, such as screws, rivets, or adhesive for example. In other embodiments, the base 24 of the finger body 20 may also be attached to the substrate. The control system 100 also includes separate closed-loop current control circuits 100A-B, whereby circuit 100A is used to control the extensor actuator 30 and the circuit 100B is used to control the flexor actuator 40, as shown in FIG. 6. It should be appreciated that the control circuit 100B, which is used to control the movement of the flexor actuator 40 is structurally equivalent to the control circuit 100A discussed in detail herein. Thus, in the case of the control circuit 100A, only the extensor actuator 30 and the associated current sensor 260A is coupled to the circuit 100A, and in the case of the control circuit 100B, only the flexor actuator 40 and the associated sensor 260B is coupled to the circuit 100A. Thus, for the sake of brevity, only the control circuit 100A will be discussed below. Specifically, the control circuit 100A includes an operational amplifier 400, such as model LM324 provided by Texas Instruments. The operational amplifier 400 includes an inverting terminal 410, a non-inverting terminal 420, and an output terminal 430. The inverting terminal 410 is coupled to the output of the hall-effect sensor 260A, while the non-inverting terminal 420 is coupled to a control voltage source 450, which applies a voltage Vi thereto. The control voltage source 450 may comprise any suitable voltage source, such as a microprocessor controlled voltage source, which is programmed to control the voltage magnitude applied as voltage Vi to the non-inverting terminal 420, which is supplied by an antagonistic position controller 500 to be discussed. For example, the control voltage source 450 may comprise any suitable prosthetic control interface, which is used to initiate the movement of the prosthetic finger 10. Coupled to a node 460 between the voltage source 450 and the non-inverting terminal 420 is a resistor 462, such as a 1 M Ohm resistor. The output terminal 430 of the op-amp 400 is coupled to one end of a resistor 465, such as a 100 K Ohm resistor, while the other end of the resistor 465 is coupled to a gate terminal 470 of a transistor 480, such as a metal oxide field effect transistor (MOSFET), however any other suitable transistor may be used. For example, the transistor 480 may comprise a MOSFET model NTE2389 that is provided by NTE Electronics, Inc. In addition, a capacitor 482, such as a 0.1 uF capacitor, is coupled at one end at a node 484 that is between the resistor 465 and the gate terminal 470, while the other end of the capacitor 482 is coupled to ground. As such, the capacitor 482 operates as a passive low-pass filter, which attenuates any noise at that gate terminal 470 of the transistor 480. The transistor 480 includes a drain terminal 490 that is coupled to a DC (direct current) voltage source 492, such as a 5 V voltage source; however, the DC voltage source 492 may provide any suitable DC voltage magnitude. In addition, the transistor 480 also includes a source terminal 494 that is coupled to the elongated section 130 of actuator 30, while the other elongated section 120 of the actuator 30 is coupled in series with the input of the hall-effect current sensor 260A, while the end 150 of the elongated section 120 is coupled to ground. Thus, the current sensor 260A is positioned in series with the elongated section 120 of the actuator 30 to monitor the current flowing therethrough.

Thus, the voltage Vi supplied by voltage source 450 under control of the position controller 500 (i.e. i=E or F, where $V_E$ is the voltage applied to the extensor current controller 100A; and $V_F$ is the voltage applied to the flexor current controller 100B) is proportional to the current flow $I_i$ that is desired to be passed through the SMA actuators 30 and 40. The electrical current $I_i$ (i.e. i=E or F, where $I_E$ is the electrical current applied to the extensor actuator 30; and $I_F$ is the electrical current applied to the flexor actuator 40) is measured by the hall-effect sensor 260A, in the case of actuator 30, and measured by hall-effect sensor 260B, in the case of actuator 40, which is then proportionally converted into a voltage, which operates as a feedback, and supplied to the inverting terminal 410 of the operational amplifier 400. That is, $V_E$ and $V_F$ are the voltage inputs to the respective current controllers 100A and 100B, which Joule heat the respective extensor and flexor SMA actuators 30 and 40 to generate respective electrical currents $I_E$ and $I_F$.

Figure 7:
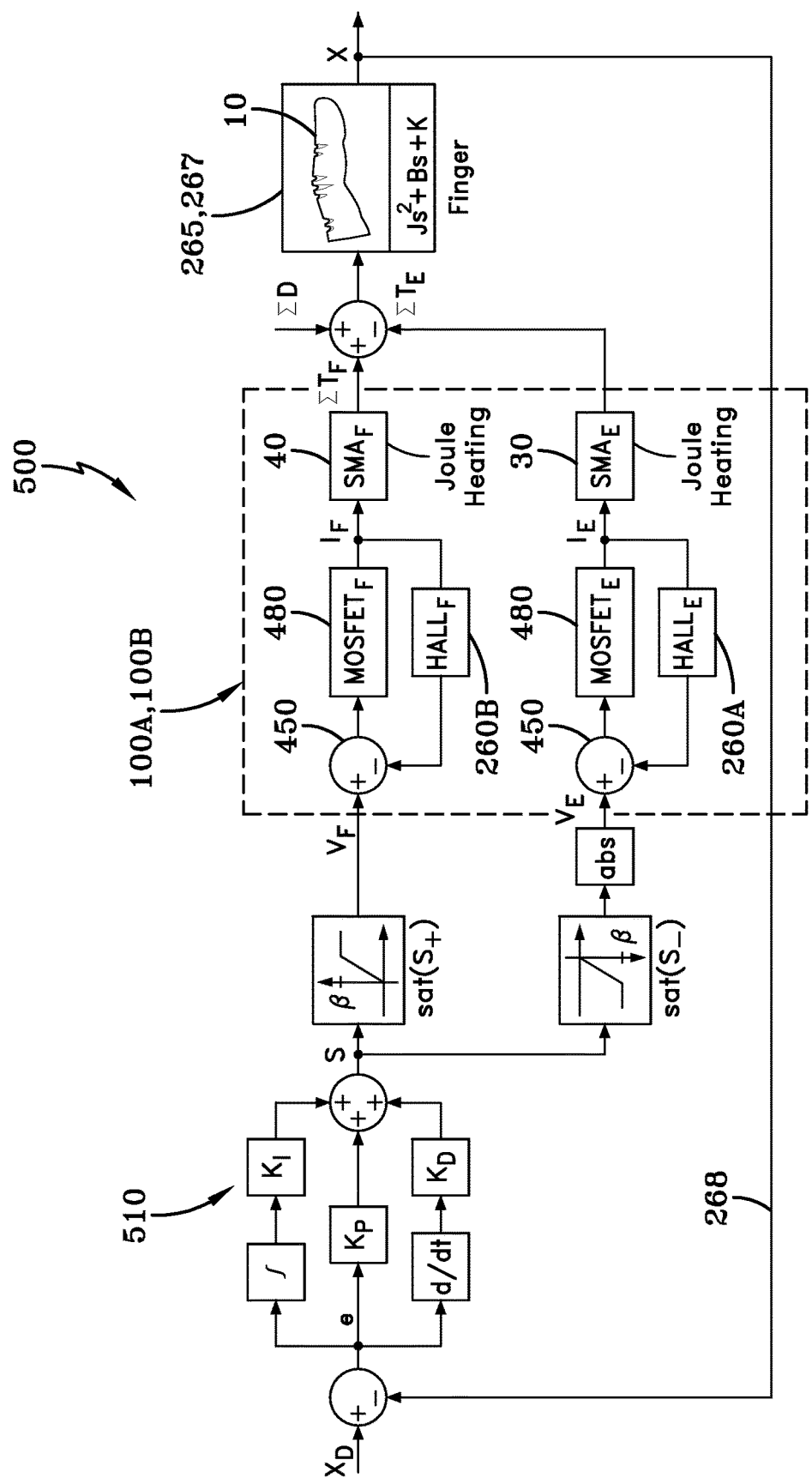
FIG. 7 is a schematic diagram of a non-linear position control system, which utilizes the current control circuits of FIG. 6, to control the movement of the extensor actuator and the flexor actuator of the prosthetic finger in accordance with the concepts of the present invention.

In order to control the operation of the prosthetic finger 10, the antagonistic position controller 500 is utilized, as shown in FIG. 7. The antagonistic position controller 500 is based on a lumped parameters approach to model the combined system, which includes the prosthetic finger 10 and the current controllers 100A-B. However, it should be appreciated that any suitable modeling technique may be used. In particular, using the lump parameters technique, the combined system is modeled by the equation: $\Sigma T_F -$ $\Sigma T_E = j\ddot{X} = B\dot{X} + KX + \Sigma D = G_F H_F V_F - G_E H_E V_E$, hereinafter referred to as "Eq. 1", where $T_F$ and $T_E$ are the torques applied by the flexor and extensor SMA actuators, respectively. In addition, J, B and K are respectively the effective inertia, damping and stiffness of the prosthetic finger 10, which includes the skin, sensors, environment/object in contact with the prosthetic finger 10. Disturbances (D) can also be applied to the prosthetic finger 10 in an unpredictable way. In addition, the stiffness of the SMA actuators 30 and 40 is subject to change, as well when the actuators 30, 40 are heated above their respective phase transition temperatures. The variable "X" is the angular displacement of the prosthetic finger 10, which is generated by the hall-effect position sensor 265. $V_E$ and $V_F$ are the voltage inputs to the current controllers 100A and 100B that Joule heat the extensor actuator 30 and the flexor actuator 40. $G_F$ and $G_E$ define the non-linear relationships between the voltage inputs $V_i$ and the electrical current outputs $I_i$ of the controllers 100A and 100B.

Thus, during operation of the prosthetic finger 10, the current controllers 100A and 100B Joule heat their respective extensor and flexor SMA actuators 30 and 40 above their phase transition temperatures so that they actuate and apply their respective torques ($T_E$ and $T_F$) to the finger environment system in opposite directions. In addition to being Joule heated, each SMA actuator 30 and 40 is liquid cooled, by any suitable liquid, such as water. In the case where the SMA actuators 30 and 40 are water cooled by submerging the prosthetic finger 10 into a water environment, the cooling that is imparted to the SMA actuators 30, 40 is not directly controlled, but rather occurs passively as the flexion and extension movements of the prosthetic finger 10 take place. This action forces water to flow into and out of the insulating tubes 240 that are associated with each actuator 30 and 40, via the ports 250 disposed at the tip 22 of the prosthetic finger 10. Accordingly, the nonlinear dynamics representing the relationships between Joule heating and water cooling of the extensor and flexor actuators 30 and 40 to the respective torques they apply are $H_E$ and $H_F$. As such, to control the prosthetic finger 10, the present invention utilizes the non-linear position controller 500, which includes two inner current control loops 100A-B, which are embedded within an outer non-linear PID (proportional-integral-derivative) position feedback control loop 510, as shown in FIG. 7. Thus, the difference between the desired finger posture $X_D$ and the measured finger posture X is formed as $e = X_D - X$. It should be appreciated that the position X, is measured by the hall-effect position sensor 265 and magnet 267. Thus, as the finger 10 flexes and extends, the distance between the position sensor 265 and the magnet 267 changes; and this change in distance is resultantly measured by the position sensor 265 as the "X" position value. This "X" value, which identifies the position of the finger 10 is then supplied to the control loop 510 of position controller 500, whereupon the voltage Vi (i.e. $V_E$ and $V_F$) are adjusted as necessary.

In addition, an error manifold is formed as $S = K_p e + K_I \int e \, dt + K_D \dot{e}$. In order to minimize the tracking error "e", saturation functions are used to permit high gains without overheating and damaging the actuators 30 and 40. Thus, through the thermomechanical training process, discussed above, the action of heating the flexor actuator 40 will minimize positive errors while heating the extensor will minimize negative tracking errors because the actuators apply torques in opposing directions. Thus, $V_E$ and $V_F$ will never be active simultaneously. Furthermore, the control law for each of the actuators 30 and 40 is defined by:

$$V_F = \beta_F sat(S), \beta_F = \begin{cases} \beta, S > 0 \\ 0, S \leq 0 \end{cases}$$

and $$V_E = \beta_F sat(S), \beta_E = \begin{cases} \beta, S < 0 \\ 0, S \geq 0 \end{cases},$$

which is graphically shown in FIG. 7. The constant $\beta$ is based on an upper bound estimate of the torques acting on the, system model defined by Eq. (1) of the prosthetic finger 10 and empirical observations concerning the maximum electrical current each actuator 30 and 40 could reasonably tolerate. Taken together, these control laws resemble a sliding mode controller with the exception that each actuator 30, 40 can only minimize positive or negative errors. It should be appreciated, that the control functions of the outer non-linear PID (proportional-integral-derivative) position feedback control loop 510 may be implemented in hardware, software, or any combination thereof. For example, the control functions may be implemented in software for execution on any suitable controller or computing device, such as a portable computing device.

It should also be appreciated that in other embodiments, the actuators 30 and 40 may be utilized without the prosthetic body 20. In such embodiments, the actuators 30 and 40 are coupled together by a rigid or flexible connecting member to enable the antagonistic flexion and extension movements. For example the actuators 30 and 40 may be coupled together, such that the end (150, 160) of actuator 30, and the end (150, 160) of actuator 40 are attached together by the rigid or flexible connecting member. It should also be appreciated that the SMA actuators 30 and 40 may be trained to take on any shape, including a rectilinear shape, a curvilinear shape, or a shape that is a combination of both, so long as the shape one actuator 30, 40 takes on in its austenite phase is antagonistic to the shape the other actuator 30, 40 takes on in its austenite phase.

In another aspect, the prosthetic finger 10 may include a thermocouple that is integrated into the finger body 20 to enable a thermal override setting to prevent unintentionally overheating the SMA actuators. In other embodiments, a compliant tactile sensor may be integrated into the finger body 20 to control the amount of force that is applied by the prosthetic finger 10.

In another embodiment, the antagonistically actuated shape memory alloy (SMA) manipulator of the present invention may comprise the SMA manipulator 700, as shown in FIG. 8. The manipulator 700 comprises a pair of hollow elongated tubes, 610 and 620. In other embodiments, the actuators 610 and 620 may comprise plates, wires, and the like, which may be hollow, solid or a combination of both. Thus, the SMA actuators 610 and 620 are trained to take on flexion shapes in their austenite phase when heated, which is similar to that of actuator 40, previously discussed. It should also be appreciated that the SMA actuators 610 and 620 may be "trained" using any desired technique.

The tube 610 is substantially linear in its martensite phase and is bounded by ends 630 and 632, and tube 620 is also substantially linear in its martensite phase and is bounded by ends 640 and 642. As such, ends 632 and 642 of the tubes 610, 620 are fluidly attached to a housing or coupler 650, which includes a conduit 652 that serves to fluidly couple the ends 632 and 642 together. In addition, the conduit 652 comprises electrically conductive material, such as copper for example. As such, the conduit 652 electrically couples the actuators 610 and 620 together. In addition, the conduit 652 also allows liquid, such as water, to enter either one of ends 630, 640, whereupon the water is permitted to flow out the other end 630,640. The coupler 650 may comprise any suitable material, such as plastic or metal. In one aspect, the tubes 610 and 620 extend from the coupler 650 so as to be substantially parallel to each other in their martensite phase, however may be configured so that they are in any desired orientation. It should also be appreciated that the tubes 630,640 may be any desired length, and have any desired cross-sectional shape, such a rectilinear shape, curvilinear shape or a combination of both. The SMA manipulator 700 also includes an SMA plate 670, which is formed of "superelastic" SMA. The plate 670 may be any desired dimension or shape, such as a rectangular or round shape for example. In one aspect, the SMA plate 670 may be "trained" to be substantially linear in shape, so as to be in an extension orientation in its martensite phase, when cooled, as shown in FIG. 8. However, the plate 670 may be trained to take on any desired shape in its martenistic phase. Thus, the SMA plate 670 serves to act as a spring, and as such serves to provide the extension movement, which is antagonistic to the flexion movement of the actuators 610 and 620. The plate 670 has ends 672 and 674, such that end 674 is attached to the coupler 650.

It should also be appreciated that in some embodiments, the free ends 630, 640 of the actuators 610, 620 may be attached to a rigid or flexible coupler. In other embodiments, the actuators 610,620 may comprise SMA wires, films, tapes, and ribbons.

Thus, during operation of the manipulator 700, water or other cooling liquid is permitted to flow through the tubes 610 and 620 using any suitable technique. For example, a pump may be used to force cooling water through the tubes 610, 620, or water may move through the tubes 610, 620 freely when submerged in a body of water. In addition, electrical current is applied to the actuators 610 and 620 causing them to be heated. As the actuators 610 and 620 are heated, they enter their austenite phase and take on their flexed shape. The act of flexion by the actuators 610, 620 causes them to engage and bend the extensor plate 670, such that the actuators 610, 620 and 670 are in a flexed state. When the flexor actuators 610, 620 are cooled, the extensor actuator 670 acts as a spring and assists in urging the flexor actuators 610, 620 back to an extension position, as shown in FIG. 8. It should be appreciated that the electrical current used to heat the flexor actuators 610, 620 may comprise any suitable electrical current applying device. Furthermore, it should be appreciated that any heating method can be used, such as a flame.

It is also contemplated that in other embodiments of the manipulator the present invention, any number of extensor and flexor actuators may be used. In addition, the number of extensor and flexor actuators may be combined in any desired manner, such that the number of extensor actuators may be equal to, less than, or more than the number of flexor actuators that are used in the manipulator.

Therefore, one advantage of the present invention is that an antagonistically actuated shape memory alloy (SMA) manipulator comprises a device that allows a more rapid motion in flexion and extension than that which is achieved with conventional SMA actuators, which utilize a return spring mechanism. Still another advantage of the present invention, is that an antagonistically actuated shape memory alloy (SMA) manipulator enables forces to be actively applied in both directions of actuation, whereas conventional SMA actuators utilize biasing elements or spring return mechanisms that allow the application of active forces in only one direction. Yet another advantage of the present invention is that an antagonistically actuated shape memory alloy (SMA) manipulator is capable of being used in underwater environments, including underwater applications, such as deep sea exploration, rescue missions, and salvage operations. Another advantage of the of antagonistically actuated SMA manipulator, is that SMA tubes can be used which allows the SMA manipulator to have an enclosed cooling system to permit a more rapid system response, which is particularly useful in land based robotics applications, such as prosthetic hands.

Thus, it can be seen that the objects of the present invention have been satisfied by the structure and its method for use presented above. While in accordance with the Patent Statutes, only the best mode and preferred embodiments have been presented and described in detail, with it being understood that the present invention is not limited thereto or thereby. Accordingly, for an appreciation of the true scope and breadth of the invention, reference should be made to the following claims.

What is claimed is:

1. A prosthetic device comprising:
a prosthetic hand having a plurality of flexible fingers, wherein one or more of said fingers includes:
a first shape memory alloy (SMA) actuator configured to take on a predetermined shape when in an austenite phase, said first SMA actuator including:
a first SMA section;
a first cavity disposed in said finger to receive at least a portion of said first SMA section; and
a first port that opens from outside of said finger and that is fluidly coupled to said first cavity, said first cavity adapted to receive a fluid via said first port; and
a second shape memory alloy (SMA) actuator configured to take on a predetermined shape when in an austenite phase, said second SMA actuator including:
a second SMA section;
a second cavity disposed in said finger to receive at least a portion of said second SMA section; and
a second port that opens from outside of said finger and that is fluidly coupled to said second cavity, said second cavity adapted to receive a fluid via said second port;
wherein the predetermined shape of said first SMA actuator in the austenite phase is antagonistic to the predetermined shape of said second SMA actuator in the austenite phase.

2. The prosthetic device of claim 1, wherein one end of said first shape memory alloy (SMA) actuator and one end of said second shape memory alloy actuator are coupled to a connecting member.

3. The prosthetic device of claim 2, wherein said connecting member is flexible.

4. The prosthetic device of claim 2, wherein said connecting member is rigid.

5. The prosthetic device of claim 1, wherein said first SMA section is selected from the group consisting of a tube, wire, film, tape, or ribbon.

6. The prosthetic device of claim 1, wherein said second SMA section is selected from the group consisting of a tube, wire, film, tape, or ribbon.

7. The prosthetic device of claim 1, wherein said predetermined shape of said first SMA actuator is an extension shape, and said predetermined shape of said second SMA actuator is a flexed shape.

8. The prosthetic device of claim 1, further comprising:
a controller coupled to said first SMA actuator and said second SMA actuator to place either said first SMA actuator or said second SMA actuator into the austenite phase.

9. The prosthetic device of claim 1, wherein said first SMA actuator comprises a plurality of SMA actuators.

10. The prosthetic device of claim 1, wherein said second SMA actuator comprises a plurality of SMA actuators.

11. The prosthetic device of claim 1, wherein said first SMA actuator comprises a plurality of SMA actuators, and said second SMA actuator comprises a plurality of SMA actuators, such that the number of first SMA actuators is different from the number of second SMA actuators.

12. The prosthetic device of claim 1, wherein said first SMA section and said second SMA section are arranged in a stacked configuration.

13. The prosthetic device of claim 1, wherein said first and second SMA sections each include a pair of parallel and spaced apart elongated sections that are joined together at one end that is positioned proximate to said first and second ports, respectively, and wherein the free ends of said elongated sections are adapted to be coupled to a controller.

14. The prosthetic device of claim 1, wherein when said first SMA actuator is in the austenite phase said second SMA actuator is in a martensite phase, and vice versa.

15. The prosthetic device of claim 1, further comprising:
a first hall-effect sensor and a first magnet positioned adjacent to said first SMA section; and
a second hall-effect sensor and a second magnet positioned adjacent to said second SMA section.

16. A prosthetic device comprising:
a flexible finger having a first cavity and a second cavity, wherein each said cavity includes an opening that opens to the outside of the finger to receive fluid into said cavity;
an extensor actuator including a section of SMA material, at least partially disposed in said first cavity, said SMA material of said extensor actuator disposed in said first cavity; and
a flexor actuator including a section of SMA material, at least partially disposed in said second cavity, said SMA material of said flexor actuator disposed in said second cavity;
wherein said extensor actuator and said flexor actuator have trained phases that are configured to selectively move said finger to an extended position or to a flexed position, respectively.

17. The prosthetic device of claim 16, wherein said trained phases are controlled by the application of the fluid in one of said first or second cavities.

18. The prosthetic device of claim 16, wherein said flexible finger includes a plurality flexible fingers that are included in a prosthetic hand.

19. A method of controlling a prosthetic device comprising:
providing a prosthetic hand having a plurality of fingers, each said finger having a first cavity with a first smart metal alloy (SMA) section disposed therein, said first cavity having a first opening on the outside of said finger, and providing a second cavity with a second SMA section disposed therein, said second cavity having a second opening on the outside of said finger;
heating one or more of said first SMA sections to move said associated fingers into a first positional state; and
applying said fluid into said first cavity via said first opening to cool the temperature of said one or more heated first SMA sections to release said first positional state.

20. The method of claim 19, further comprising:
heating one or more of said second SMA sections to move said associated fingers into a second positional state.

21. The method of claim 20, further comprising:
applying said fluid into said second cavity via said second opening to cool the temperature of said one or more heated second SMA sections to release said second positional state.

22. The method of claim 20, wherein said first positional state and said second positional state are antagonistic to one another.

* * * * *